(12) United States Patent
Chin et al.

(10) Patent No.: US 7,544,203 B2
(45) Date of Patent: Jun. 9, 2009

(54) TEMPORARY SEAL AND METHOD FOR FACILITATING ANASTOMOSIS

(75) Inventors: Albert K Chin, Palo Alto, CA (US); Dwight Morejohn, Davis, CA (US); Charles S Taylor, San Francisco, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 864 days.

(21) Appl. No.: 10/952,392

(22) Filed: Sep. 27, 2004

(65) Prior Publication Data

US 2006/0206121 A1    Sep. 14, 2006

Related U.S. Application Data

(63) Continuation of application No. 10/033,614, filed on Dec. 26, 2001, now Pat. No. 6,814,743, which is a continuation-in-part of application No. 10/123,470, filed on Apr. 15, 2002.

(51) Int. Cl.
    *A61B 17/08* (2006.01)
(52) U.S. Cl. .................. 606/213; 606/151; 606/153; 606/157; 606/159
(58) Field of Classification Search ............. 606/213, 606/215, 151, 153, 157, 159
    See application file for complete search history.

(56) References Cited

U.S. PATENT DOCUMENTS

| | | | |
|---|---|---|---|
| 1,052,374 A | 2/1913 | Parr | |
| 1,867,624 A | 7/1932 | Hoffman | |
| 2,850,007 A | 9/1958 | Lingley | |
| 2,919,692 A | 1/1960 | Ackermann | |
| 3,104,666 A | 9/1963 | Hale et al. | |
| 3,253,594 A | 5/1966 | Matthews et al. | |
| 3,254,650 A | 6/1966 | Collito | |
| 3,394,699 A | 7/1968 | Koett | |
| 3,561,429 A | 2/1971 | Jewett | |

(Continued)

FOREIGN PATENT DOCUMENTS

AU           270419           5/1965

(Continued)

OTHER PUBLICATIONS

Mahieu, F.M. et al., "Use of the Brock Punch for Confection of a Shunt Between Ventricles, A Ventricle and Pulmonary Artery or a Ventricle and the Aorta Without Cardio-Pulmonary By-Pass (CPS)," Acta Chirurgica Belgica, Belgian Surgical Society, Mar. 1975, No. 2, pp. 160-164.

(Continued)

*Primary Examiner*—(Jackie) Tan-Uyen T. Ho
*Assistant Examiner*—Jing Ou
(74) *Attorney, Agent, or Firm*—Fenwick & West LLP

(57) ABSTRACT

Forming a proximal anastomosis on an aortic wall includes method and instrumentation and apparatus for forming an aortic puncture and inserting a fluid-impervious sealing element with a lateral flange and central stem into the vessel through the puncture. An anastomosis of a graft vessel over the puncture is partially completed with the central stem of the sealing element protruding through the partial anastomosis. A removal instrument attaches to the central stem and retrieves the sealing element that disassembles in helical disassociation of the flange and stem into a continuous strand that is withdrawn from the partial anastomosis prior to completion of the procedure.

6 Claims, 5 Drawing Sheets

U.S. PATENT DOCUMENTS

| | | | |
|---|---|---|---|
| 3,628,524 A | 12/1971 | Jamshidi | |
| 3,683,891 A | 8/1972 | Eskridge et al. | |
| 3,774,615 A | 11/1973 | Lim et al. | |
| 3,776,623 A | 12/1973 | Hill et al. | |
| 3,874,388 A * | 4/1975 | King et al. | 606/232 |
| 3,882,849 A | 5/1975 | Jamshidi | |
| 3,993,078 A | 11/1976 | Bergentz et al. | |
| 4,010,543 A | 3/1977 | Nusbaum | |
| 4,010,737 A | 3/1977 | Vilaghy et al. | |
| 4,018,228 A | 4/1977 | Goosen | |
| 4,122,855 A | 10/1978 | Tezel | |
| 4,216,776 A | 8/1980 | Downie et al. | |
| 4,243,048 A | 1/1981 | Griffin | |
| 4,282,884 A | 8/1981 | Boebel | |
| 4,314,565 A | 2/1982 | Lee | |
| 4,352,358 A | 10/1982 | Angelchik | |
| 4,388,925 A | 6/1983 | Burns | |
| 4,469,109 A | 9/1984 | Melh | |
| D281,721 S | 12/1985 | Scanlan | |
| 4,682,606 A | 7/1987 | DeCaprio | |
| 4,699,154 A | 10/1987 | Lindgren | |
| 4,721,109 A | 1/1988 | Healey | |
| 4,733,671 A | 3/1988 | Mehl | |
| 4,738,261 A | 4/1988 | Enstrom | |
| 4,744,364 A | 5/1988 | Kensey | |
| 4,753,637 A | 6/1988 | Horneffer | |
| 4,785,826 A | 11/1988 | Ward | |
| 4,794,928 A | 1/1989 | Kletschka | |
| 4,852,568 A | 8/1989 | Kensey | |
| 4,921,478 A | 5/1990 | Solano et al. | |
| 4,931,042 A | 6/1990 | Holmes et al. | |
| 4,961,430 A | 10/1990 | Sheahon | |
| 5,005,585 A | 4/1991 | Mazza | |
| 5,018,530 A | 5/1991 | Rank et al. | |
| 5,108,420 A * | 4/1992 | Marks | 606/213 |
| 5,108,421 A | 4/1992 | Fowler | |
| 5,116,357 A | 5/1992 | Eberbach | |
| 5,122,122 A | 6/1992 | Allgood | |
| 5,129,913 A | 7/1992 | Ruppert | |
| 5,147,374 A | 9/1992 | Fernandez | |
| 5,172,702 A | 12/1992 | Leigh et al. | |
| 5,176,687 A | 1/1993 | Hasson et al. | |
| 5,192,294 A | 3/1993 | Blake, III | |
| 5,192,301 A | 3/1993 | Kamiya et al. | |
| 5,197,971 A | 3/1993 | Bonutti | |
| 5,222,974 A | 6/1993 | Kensey et al. | |
| 5,258,000 A | 11/1993 | Gianturco | |
| 5,273,519 A | 12/1993 | Koros et al. | |
| 5,290,249 A | 3/1994 | Foster et al. | |
| 5,304,193 A | 4/1994 | Zhadanov | |
| 5,312,417 A | 5/1994 | Wilk | |
| 5,312,435 A | 5/1994 | Nash et al. | |
| 5,313,958 A | 5/1994 | Vauer | |
| 5,330,446 A | 7/1994 | Weldon et al. | |
| 5,330,497 A | 7/1994 | Freitas et al. | |
| 5,342,393 A | 8/1994 | Stack | |
| 5,350,399 A | 9/1994 | Erlebacher et al. | |
| 5,383,896 A | 1/1995 | Gershony et al. | |
| 5,383,897 A | 1/1995 | Wholey | |
| 5,395,383 A | 3/1995 | Adams et al. | |
| 5,397,331 A * | 3/1995 | Himpens et al. | 606/151 |
| 5,403,338 A | 4/1995 | Milo | |
| 5,413,571 A | 5/1995 | Katsaros et al. | |
| 5,423,330 A | 6/1995 | Lee | |
| 5,454,833 A * | 10/1995 | Boussignac et al. | 606/213 |
| 5,470,320 A | 11/1995 | Tiefenbrun et al. | |
| 5,488,958 A | 2/1996 | Topel et al. | |
| 5,496,332 A | 3/1996 | Sierra et al. | |
| 5,515,861 A | 5/1996 | Smith | |
| D372,310 S | 7/1996 | Hartnett | |
| 5,545,178 A | 8/1996 | Kensey et al. | |
| 5,593,422 A | 1/1997 | Muijs Van de Moer et al. | |
| 5,620,461 A | 4/1997 | Muijs Van De Moer et al. | |
| 5,630,833 A | 5/1997 | Katsaros et al. | |
| 5,634,936 A | 6/1997 | Linden et al. | |
| 5,688,286 A | 11/1997 | Yoon | |
| 5,690,674 A | 11/1997 | Diaz | |
| 5,695,504 A | 12/1997 | Gifford, III et al. | |
| 5,700,277 A | 12/1997 | Nash et al. | |
| 5,702,412 A | 12/1997 | Popov et al. | |
| 5,746,760 A | 5/1998 | Humphrey, Jr. | |
| 5,749,883 A | 5/1998 | Halpern | |
| 5,766,220 A | 6/1998 | Moenning | |
| 5,772,986 A | 6/1998 | Kross | |
| 5,782,860 A | 7/1998 | Epstein et al. | |
| 5,788,651 A | 8/1998 | Weilandt | |
| 5,797,933 A | 8/1998 | Snow et al. | |
| 5,817,113 A | 10/1998 | Gifford, III et al. | |
| 5,826,251 A | 10/1998 | Kiendl | |
| 5,827,316 A | 10/1998 | Young et al. | |
| 5,865,802 A | 2/1999 | Yoon et al. | |
| 5,881,943 A | 3/1999 | Heck et al. | |
| 5,893,369 A | 4/1999 | LeMole | |
| 5,904,697 A | 5/1999 | Gifford, III et al. | |
| 5,910,153 A | 6/1999 | Mayenberger | |
| 5,944,730 A | 8/1999 | Nobles et al. | |
| 5,984,940 A | 11/1999 | Davis et al. | |
| 6,007,495 A | 12/1999 | Matula | |
| 6,010,517 A * | 1/2000 | Baccaro | 606/151 |
| 6,022,367 A | 2/2000 | Sherts | |
| 6,036,710 A | 3/2000 | McGarry et al. | |
| 6,080,173 A | 6/2000 | Williamson, IV et al. | |
| 6,080,175 A | 6/2000 | Hogendijk | |
| 6,080,176 A | 6/2000 | Young | |
| 6,093,154 A | 7/2000 | Burek et al. | |
| 6,110,187 A | 8/2000 | Donion | |
| 6,142,955 A | 11/2000 | Farascioni et al. | |
| 6,156,050 A | 12/2000 | Davis et al. | |
| 6,168,623 B1 | 1/2001 | Fogarty et al. | |
| 6,171,319 B1 | 1/2001 | Nobles et al. | |
| 6,171,321 B1 | 1/2001 | Gifford, III et al. | |
| 6,171,329 B1 * | 1/2001 | Shaw et al. | 606/213 |
| 6,174,322 B1 * | 1/2001 | Schneidt | 606/213 |
| 6,176,413 B1 | 1/2001 | Heck et al. | |
| 6,180,848 B1 * | 1/2001 | Flament et al. | 623/11.11 |
| 6,183,486 B1 | 2/2001 | Snow et al. | |
| 6,214,022 B1 | 4/2001 | Taylor et al. | |
| 6,214,029 B1 * | 4/2001 | Thill et al. | 606/213 |
| 6,248,119 B1 | 6/2001 | Solem | |
| 6,273,861 B1 | 8/2001 | Bates et al. | |
| 6,280,460 B1 | 8/2001 | Bolduc et al. | |
| 6,371,964 B1 | 4/2002 | Vargas et al. | |
| 6,371,965 B2 | 4/2002 | Gifford, III et al. | |
| 6,375,671 B1 * | 4/2002 | Kobayashi et al. | 606/213 |
| 6,387,105 B1 | 5/2002 | Gifford, III et al. | |
| 6,395,015 B1 | 5/2002 | Borst et al. | |
| 6,409,739 B1 | 6/2002 | Nobles et al. | |
| 6,416,527 B1 | 7/2002 | Berg et al. | |
| 6,428,555 B1 | 8/2002 | Koster, Jr. | |
| 6,443,965 B1 | 9/2002 | Gifford, III et al. | |
| 6,451,034 B1 | 9/2002 | Gifford, III et al. | |
| 6,464,712 B1 | 10/2002 | Epstein et al. | |
| 6,488,636 B2 | 12/2002 | Bryan et al. | |
| 6,491,704 B2 | 12/2002 | Gifford, III et al. | |
| 6,491,705 B2 | 12/2002 | Gifford, III et al. | |
| D472,318 S | 3/2003 | Solem | |
| 6,537,300 B2 * | 3/2003 | Girton | 606/213 |
| 6,616,684 B1 * | 9/2003 | Vidlund et al. | 606/213 |
| 6,652,555 B1 | 11/2003 | VanTassel et al. | |
| 6,814,743 B2 | 11/2004 | Chin et al. | |
| 2001/0000903 A1 | 5/2001 | Heck et al. | |
| 2001/0001122 A1 | 5/2001 | Gifford, III et al. | |
| 2001/0001825 A1 * | 5/2001 | Snow et al. | |
| 2001/0004697 A1 * | 6/2001 | Blatter et al. | |

| | | | | | | |
|---|---|---|---|---|---|---|
| 2001/0004698 A1* | 6/2001 | Blatter et al. | | EP | 0882429 A1 | 12/1998 |
| 2001/0016749 A1* | 8/2001 | Blatter et al. | | EP | 0894475 A1 | 2/1999 |
| 2001/0021856 A1* | 9/2001 | Bolduc et al. | | EP | 1088519 A1 | 4/2001 |
| 2001/0023354 A1* | 9/2001 | Blatter et al. | | SU | 125870 | 5/1960 |
| 2001/0037129 A1* | 11/2001 | Thill .................. 606/213 | | WO | WO 92/08513 A1 | 5/1992 |
| 2001/0047179 A1* | 11/2001 | Gifford, III et al. | | WO | WO 92/12676 A2 | 8/1992 |
| 2002/0019643 A1* | 2/2002 | Gifford, III et al. | | WO | WO 96/25886 A1 | 8/1996 |
| 2002/0029007 A1* | 3/2002 | Bryan et al. | | WO | WO 97/13463 A1 | 4/1997 |
| 2002/0029049 A1* | 3/2002 | Gifford, III et al. | | WO | WO 98/47261 A1 | 12/1997 |
| 2002/0029050 A1* | 3/2002 | Gifford, III et al. | | WO | WO 98/07399 A1 | 2/1998 |
| 2002/0038127 A1* | 3/2002 | Blatter et al. | | WO | WO 98/42262 A1 | 10/1998 |
| 2002/0042623 A1* | 4/2002 | Blatter et al. | | WO | WO 99/40851 A1 | 8/1999 |
| 2002/0065474 A1* | 5/2002 | Viola | | WO | WO 99/62415 A1 | 12/1999 |
| 2002/0077637 A1* | 6/2002 | Vargas et al. | | WO | WO 00/56226 A1 | 9/2000 |
| 2002/0082614 A1* | 6/2002 | Logan et al. | | WO | WO 00/59380 A2 | 10/2000 |
| 2002/0082626 A1* | 6/2002 | Donohoe et al. | | WO | WO 00/69346 A1 | 11/2000 |
| 2002/0087175 A1* | 7/2002 | Gifford, III et al. | | WO | WO 00/69349 A1 | 11/2000 |
| 2002/0111619 A1 | 8/2002 | Keast et al. | | WO | WO 00/74579 A2 | 12/2000 |
| 2002/0151914 A1* | 10/2002 | Gifford, III et al. | | WO | WO 02/32293 A2 | 4/2002 |
| 2002/0173809 A1* | 11/2002 | Fleischman et al. | | WO | WO 02/32323 A2 | 4/2002 |
| 2002/0177865 A1* | 11/2002 | McIntosh | | WO | WO 02/32324 A2 | 4/2002 |
| 2002/0188317 A1 | 12/2002 | Rousseau | | WO | WO 02/47532 A2 | 6/2002 |
| 2003/0023251 A1* | 1/2003 | Gifford, III et al. | | WO | WO 02/47561 A2 | 6/2002 |
| 2003/0065347 A1* | 4/2003 | Gifford, III et al. | | WO | WO 02/058568 A1 | 8/2002 |
| 2004/0019360 A1 | 1/2004 | Farnsworth et al. | | WO | WO 02/074188 A2 | 9/2002 |
| 2005/0080439 A1 | 4/2005 | Carson et al. | | WO | WO 03/030753 A1 | 4/2003 |

FOREIGN PATENT DOCUMENTS

| | | |
|---|---|---|
| DE | 1160573 | 9/1961 |
| DE | 19650204 C2 | 6/1998 |
| EP | 0373927 A2 | 6/1990 |
| EP | 0544485 A1 | 6/1993 |

OTHER PUBLICATIONS

Murakami, T., et al., "Experience With Sequential Bypass Grafts Using a Vascular Punch," Journal of the Japanese Association For Thoracic Surgery, 35 (1), 1987, p. 20-25.

* cited by examiner

TEMPORARY SEAL AND METHOD FOR FACILITATING ANASTOMOSIS

This application is a continuation of application Ser. No. 10/033,614, filed on Dec. 26, 2001, now U.S. Pat. No. 6,814,743, which application is a continuation-in-part of application Ser. No. 10/123,470, filed on Apr. 15, 2002, which application are incorporated herein in their entireties by this reference.

FIELD OF THE INVENTION

This invention relates to coronary bypass grafting surgery and more particularly to instruments and method to facilitate performing an aortotomy and proximal anastomosis, for example, associated with coronary artery bypass grafting surgery.

BACKGROUND OF THE INVENTION

Contemporary coronary artery bypass grafting surgery is performed on a beating heart to obviate complications commonly associated with prior surgical practices of transitioning a patient onto and off of a heart-lung machine that maintained circulation while the heart was in quiescent condition during construction of a coronary arterial bypass. However, performing an aortotomy and a proximal anastomosis on the aorta that is perfused with blood under pressure contribute to substantial losses of blood in the absence of temporary measures taken to curtail blood flow through the aortic hole. Side-bite and surface-oriented clamping mechanisms have been used to diminish loss of blood during the surgical procedures of punching the aortic hole and anastomosing the graft vessel, but such temporary occlusions damage the endothelium and dislodge emboli that may migrate through the circulatory system. Alternative schemes for performing an aortotomy and limiting loss of blood during the period of anastomosing a bypass graft include introducing a plug or seal at the site of the aortotomy, but such schemes commonly inhibit convenient and rapid completion of the graft anastomosis, and present other complications to be resolved following the grafting procedure.

SUMMARY OF THE INVENTION

In accordance with the method and instrumentation of the present invention, an aorto-coronary bypass graft is performed using an aortic punch including a corkscrew instrument and a hemostatic sheath that selectively delivers and positions a seal within the punched aortic hole for retention against the aortic wall under tension established by an external structure. The suture anastomosis is performed with the hemostatic seal in place and with a central stem of the seal residing near the location of the last placed stitch. A tubular removal instrument is positioned about the protruding stem to remove the seal as a tear-away strip that is pulled through the tubular removal instrument.

DETAILED DESCRIPTION OF THE INVENTION

Figure 1:
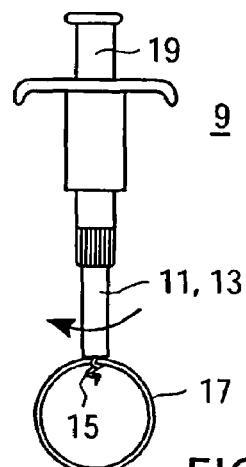
FIG. 1 is a pictorial illustration of the corkscrew aortic punch disposed for insertion into the aorta through a hemostatic sheath in accordance with one embodiment of the present invention.
Figure 2:
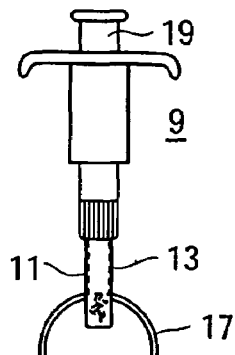
FIG. 2 is a pictorial illustration of the hemostatic sheath penetrated through the aortic wall.
Figure 3:
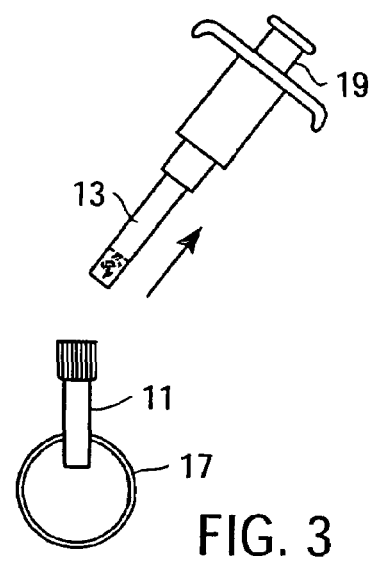
FIG. 3 is a pictorial illustration of the hemostatic sheath positioned within the aorta as the aortic punch is removed.
Figure 14:
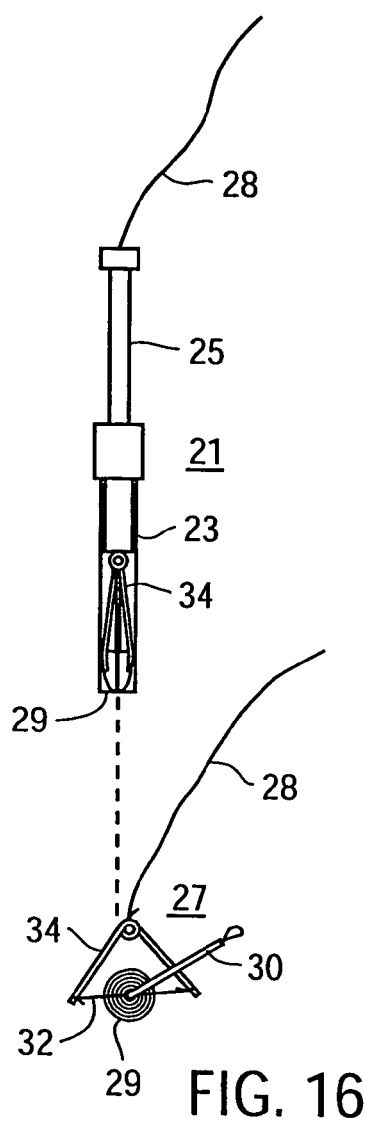
FIG. 14 is an exploded view of the aortic punch and hemostatic sheath in accordance with one embodiment of the present invention.
Figure 15:
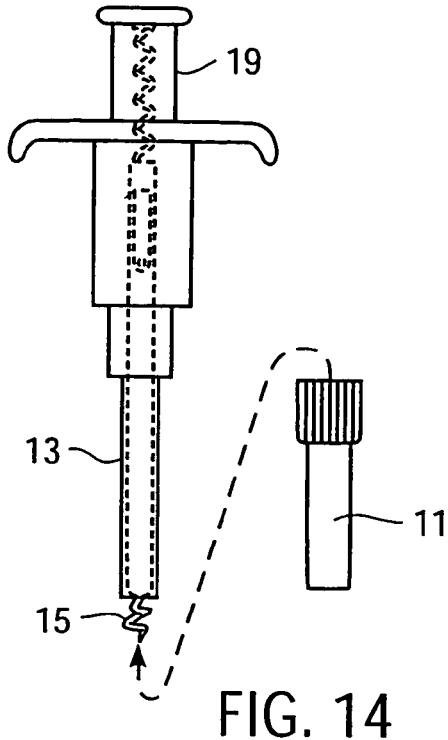
FIG. 15 is a frontal view of the assembled aortic punch and hemostatic sheath prepared for performing an aortotomy according to the present invention.

Referring now to FIGS. 1, 2 and 3, there are shown pictorial views of the aortic punch 9 configured for penetrating the aorta 17 of a patient in preparation for a proximal anastomosis of a bypass vessel to the aorta of the patient. Specifically, an outer hemostatic sheath 11 is coaxially disposed over the lower elongated segment 13 of the aortic punch which supports a corkscrew-type auger 15, as shown in FIGS. 14 and 15. The punch and auger 15 are rotated into a wall of the aorta 17 and the plunger 19 can then be depressed to penetrate the sharpened edge of the lower elongated segment 13 through the aorta wall. The punched-out segment of aorta wall remains captivated on the cork screw 15, and the hemostatic sheath 11 is positioned within the punched hole through the aorta wall. The plunger mechanism 19 and attached elongated lower segment is removed from the hemostatic sheath 11 that remains in position through the aorta wall, as shown in FIG. 3. A fluid-tight seal is included within the hemostatic sheath 11 to inhibit outflow of blood under pressure from the aorta 17 in which it is positioned.

Figure 4:
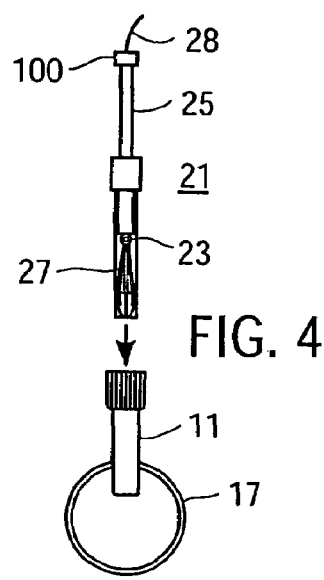
FIGS. 4 and 5 are pictorial illustrations of a seal-positioning mechanism for insertion through the hemostatic sheath into the aorta.

Referring now to the pictorial illustration of FIG. 4, there is shown a seal-insertion instrument 21 that includes a sheath 23 of outer diameter sized to slide within the hemostatic sheath 11, and a plunger 25 that is disposed to slide axially within the sheath 23 for selectively ejecting the hemostatic seal structure 27 from its confinement within the sheath 23. The hemostatic seal structure 27, as later described herein with reference to FIG. 16, includes resilient members that are confined within the sheath 23 in preparation for positioning and expansion into sealing engagement with the aorta wall, as later descried herein.

Figure 5:
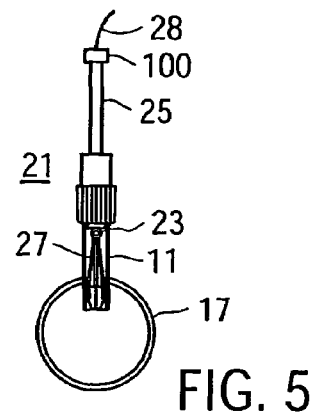
Figure 6:
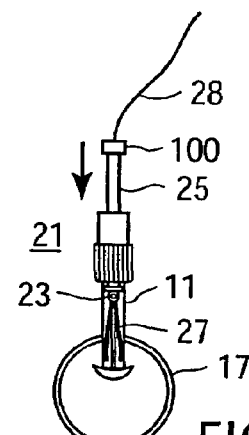
FIG. 6 is a pictorial illustration of the hemostatic seal mechanism deployed from the interior end of the hemostatic sheath.

Referring now to the pictorial illustrations of FIGS. 5 and 6, the seal-insertion instrument 21 is inserted into the hemostatic sheath 11 through the fluid-tight seal therein, and the plunger 25 is depressed to eject a portion of the hemostatic seal structure 27, within the aorta 17. The plunger 25 includes an axial lumen therethrough to pass a length of line 28 that is attached to the hemostatic seal structure 27. The proximal end of plunger 25 may also include a hemostatic seal 100 through which the length of line 28 passes.

As illustrated in FIGS. 6, 7, 16 and 17, a convex or mushroom-shaped sealing element 29 of the hemostatic seal structure 27 is deployed and manually restrained within the aorta 17 covering the punched aortic hole as the hemostatic sheath 11 and the seal-insertion instrument 21 are removed together from the aorta 17. The hemostatic seal structure 27 is thereby liberated from confinement within the seal-insertion instrument 21 to expand into sealing engagement with the aorta wall inside the punched aortic hole.

Figure 7:
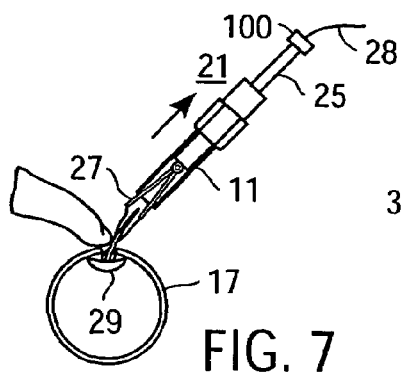
FIG. 7 is a pictorial illustration of the hemostatic seal mechanism manually positioned within the punched aortic hole as the hemostatic sheath and hemostatic seal-positioning mechanism are withdrawn.
Figure 16:
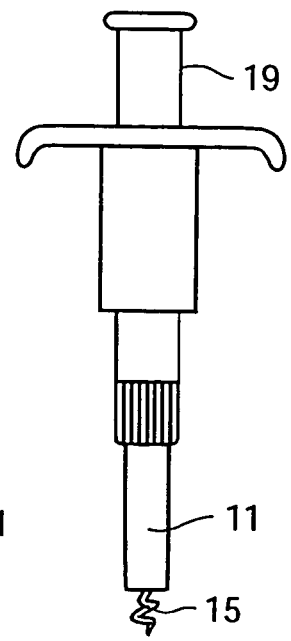
FIG. 16 is an exploded view of the hemostatic seal positioning mechanism that illustrates the hemostatic seal and tensioning structure in deployed condition and in confined condition.

Referring now to FIG. 16, the hemostatic seal structure 27 includes the convex or mushroom-shaped sealing element 29, and this sealing element 29 includes an integral central stem 30 that is attached via a suture tether 32 to a resilient frame 34 which tensions the suture tether 32. The resilient frame 34 is attached to the length of line 28 that passes through an axial lumen through the plunger 25 as the entire structure is packed in confined configuration within the hollow sheath 23 of the seal-insertion instrument 21. When ejected from the hemostatic sheath 23 upon depression of the plunger 25, the resilient frame 34 expands to tension the suture tether 32. Manual positioning by the surgeon's finger, as shown in FIG. 7, promotes proper sealing of the hole in the aorta as the resilient frame 34 expands to tension the suture tether 32. As thus positioned in this configuration, the resilient frame 34 maintains tension on the suture tether 32 that, in turn, supports the sealing element 29 from outside the aorta to provide outwardly-directed resilient biasing force on the sealing element 29. This resilient force establishes firm sealing engagement of the sealing element 29 against the inside wall of the aorta. In addition, the suture tether 32 greatly facilitates removal of the resilient frame 34, as later described herein, upon simply cutting one or both ends of the suture tether 32 away from the resilient frame 34 for removal from the sealing element 29. In one embodiment the suture-tether 32 may pass through the convex segment of the sealing element 29 to the concave side thereof on both sides of the central stem 30. In another embodiment, the suture tether 32 may be tied to the central stem 30 closely adjacent the concave surface of the sealing element 29.

Figure 17:
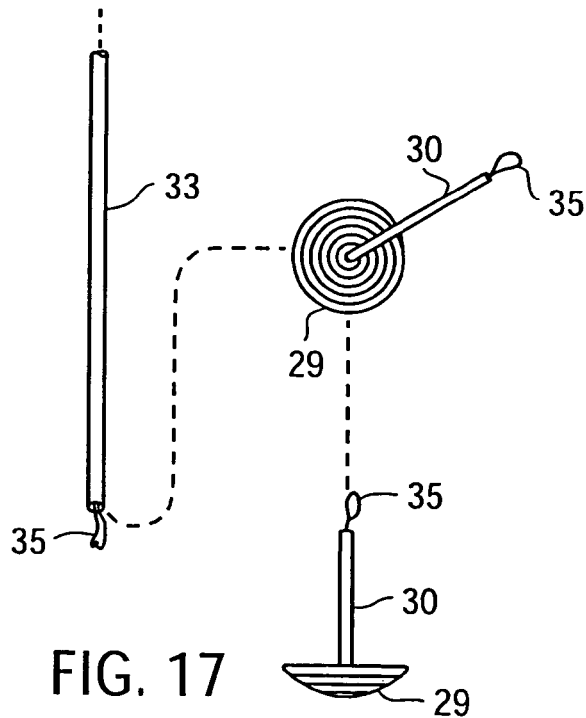
FIG. 17 is a pictorial illustration of the formation of a hemostatic seal in accordance with one embodiment of the present invention.

The sealing element 29 is formed in accordance with one embodiment of the present invention, as illustrated in FIG. 17. Specifically, a hollow tube 33 of flexible material such as polyvinyl chloride, PEBAX, or other polymer material may be extruded about a looped suture 35 or wire or other tensile member for improved tensile strength. Alternatively, a solid, flexible rod of similar material having sufficient tensile strength may be used. The hollow tube (or solid rod) 33 may be helically or spirally wound into the configuration of the mushroom-shaped sealing member 29, with the central stem 30 integrally formed thereon. The adjacent convolutes of the spirally-wound tube 33 with suture 35 or other tensile member disposed therein (or solid rod) may be lightly adhered together through the application of heat and pressure to a thermoplastic material, or through other suitable adhesive attachments to form the substantially fluid-impervious sealing element 29 that is flexible and resilient for confined packing within the hollow sheath 23 of the seal-insertion instrument 21. Light adhesion between adjacent convolutes of the spirally-wound tube 33 with a suture therein (or solid rod) promotes disassembly of the sealing element 29 as by tearing along the boundary between adjacent convolutes under tension applied to the central stem 30, as later described herein. It should be noted that the central stem 30 is an integral and continuous portion of the spiral convolutes (or other meandering pattern) that extend continuously from the central stem portion 30 to the outer perimeter of the mushroom-shaped portion of the sealing element 29. This assures substantially uniform high tensile strength of the hollow tube 33 with suture 35 disposed therein (or solid rod) over the entire continuous length of the tube 33 to assure complete removal from the aorta in the manner as later described herein. In one embodiment, the sealing element 29 may be formed by winding the hollow tube 33 (or solid rod) around a mandrel that includes separable flanges which are axially spaced apart by about the diameter dimension of the tube 33 (or solid rod), and that includes a central hollow support to house the portion that forms the central stem 30. Heat and pressure applied between such flanges causes thermoplastic flow and adhesion between adjacent convolutes in the mushroom-shaped portion and to the stem 30 in the central portion of the fluid-impervious sealing element 29 thus formed. Alternatively, bioinert adhesive may be applied to the convolutes and central stem 30 to retain the shape of the fluid-impervious sealing element 29 thus formed.

Figure 8:
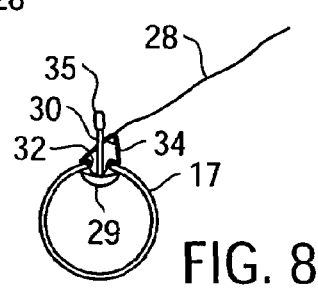
FIG. 8 is a pictorial illustration of the hemostatic seal retained in place at the punched aortic hole via an external tensioning mechanism.
Figure 9:
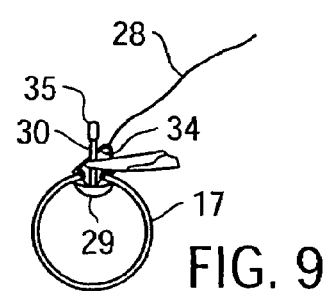
FIG. 9 is a pictorial illustration of suture anastomosis performed about the hemostatic seal.
Figure 11:
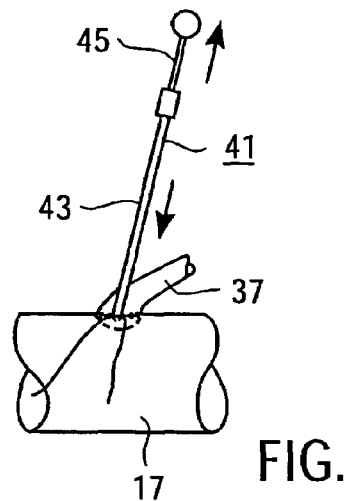
FIG. 11 is a pictorial frontal illustration of the tubular removal instrument disposed over the stem of the hemostatic seal in preparation for removal from the graft site.
Figure 10:
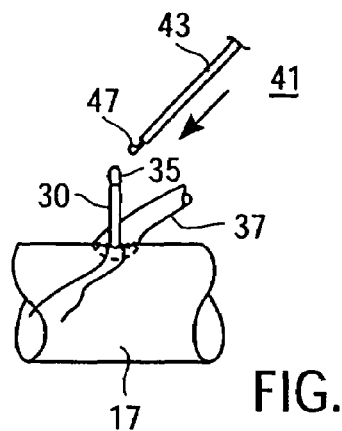
FIG. 10 is a pictorial frontal illustration of the suture anastomosis substantially completed with the stem of the hemostatic seal positioned near the last stitches.

Referring now to the pictorial illustration of FIG. 8, the sealing element 29 is shown disposed in sealing position inside the punched aortic hole with the integral stem 30 protruding through the hole, and with suture loop 35 protruding from the proximal end of the stem 30. It should be noted that the resilient frame 34 and the suture tether 32 are positioned on the outer wall of the aorta to exert an outwardly-directed force on the sealing element 29 to retain it in sealing engagement with the inner aortic wall, and to prevent inadvertent expulsion of the sealing element 29 from the hole or loss of the sealing element 29 into the aorta. The sealing element 29 is thus maintained in sealing position over the hole in the aorta during formation of the proximal anastomosis by suturing the graft vessel 37 onto the aorta 17, as shown in FIGS. 9-11. The stem 30 is flexible and can be gently pushed out of the way of sutures that are stitched about the hole in the aorta and into the proximal end of the graft vessel 37. In this way, the stem 30 is left protruding through the anastomosis at a position thereon near the last stitch (or between any adjacent stitches).

Figure 12:
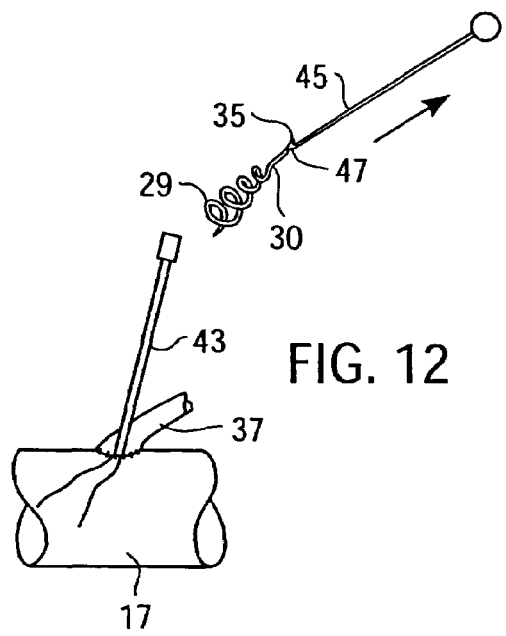
FIG. 12 is a pictorial frontal illustration of the hemostatic seal dissembled through the tubular removal instrument.
Figure 13:
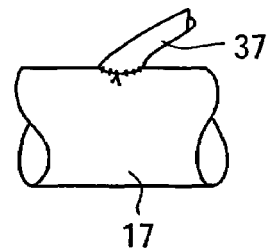
FIG. 13 is a pictorial frontal illustration of the anastomosis completed upon removal of the tubular removal instrument and tying off of the suture ends about the segment of the anastomosis from which the tubular removal instrument is withdrawn.
Figure 18:
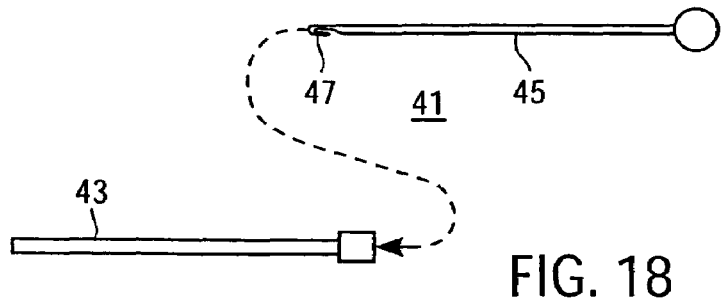
FIG. 18 is a pictorial exploded illustration of a hemostatic seal removal instrument according to one embodiment of the present invention.

Referring now to FIGS. 10-12 and 18, a seal-removal instrument 41 includes an outer tube 43 with an inner core 45 that is slidable within the outer tube 43 and that carries a hook 47 at its distal end. The assembly of inner core 45 disposed within the outer tube 43 is positioned over the stem 30 of the sealing element 29 with the hook 47 engaged in the suture loop 35. The outer tube 43 is positioned onto the stem 30 down to the root of its attachment to the mushroom-shaped spiral-wound sealing element 29, and the inner core 45 is then withdrawn from the outer tube 43. These motions cause the spirally-wound convolutes of the sealing element 29 to tear and otherwise disassemble for convenient removal as a continuous strand 29', as shown in FIG. 12, of the material from which the spirally-wound sealing element 29 was formed. Thereafter, the outer tube 43 may be withdrawn and the sutures tied off near where outer tube 43 was positioned to complete the proximal anastomosis, as shown in FIG. 13.

Alternatively, the central stem 30 may be formed as an integral part of the mushroom-shaped portion of the sealing element 29 with sufficient length to extend through the outer tube 43 adequately to permit finger gripping of the stem 30 for manual tensioning and removal of the continuous strand 29' through the outer tube 43 without the need for the hooked inner core 45 and associated suture loop 35.

Figure 19:
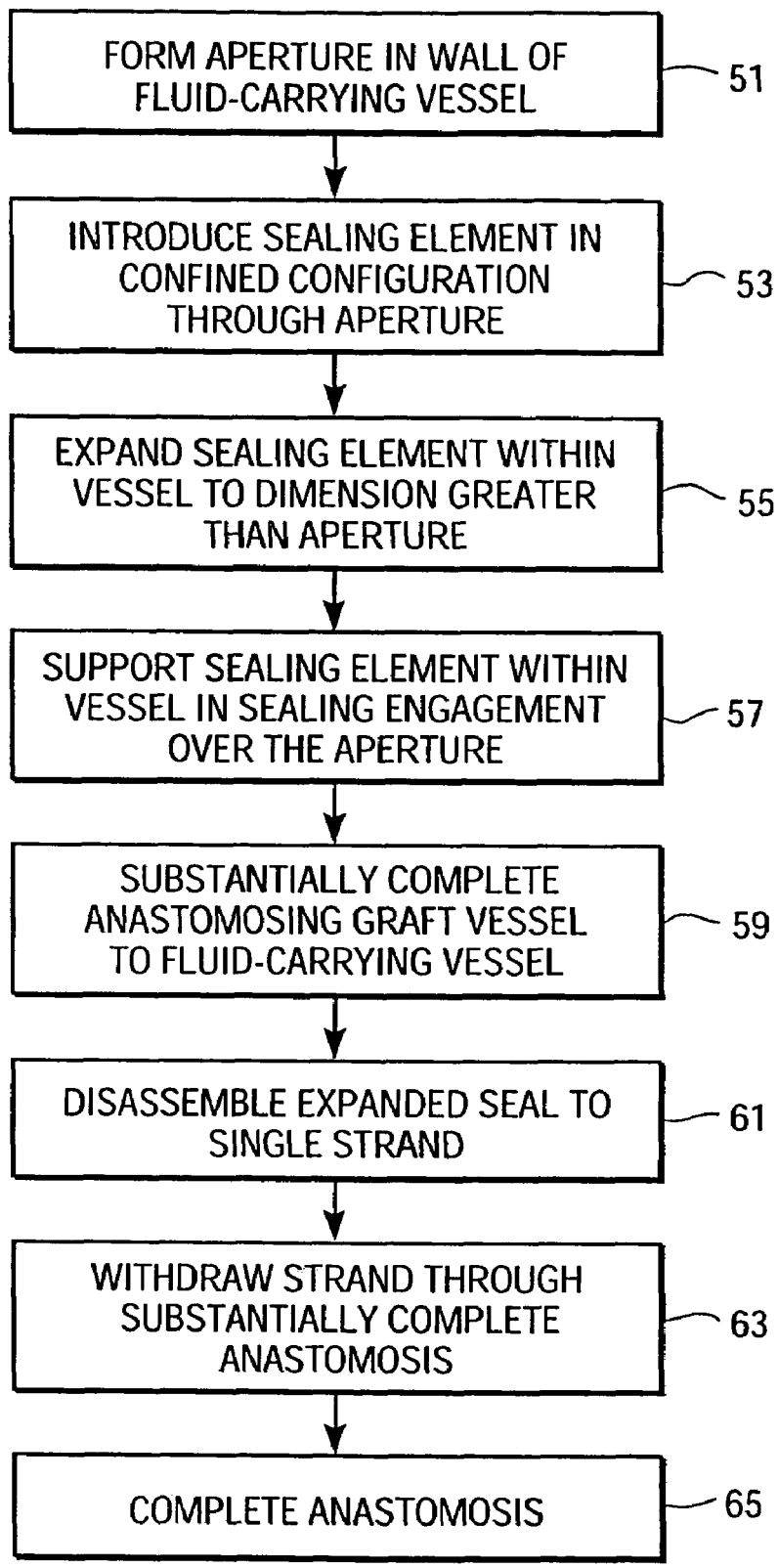
FIG. 19 is a flow chart illustrating an embodiment of the surgical process according to the present invention.

Referring now to the flow chart of FIG. 19, an embodiment of the surgical procedure performed according to the present invention includes forming an aperture 51 in the aorta wall, as illustrated in FIGS. 1 and 2. The hemostatic seal structure in confined configuration within the hemostatic sheath is then introduced 53 into the aorta through the hole in the wall thereof. The sealing element resiliently expands 55 inside the aorta to form a fluid-tight seal over the hole in the wall, and is supported 57 on a tensioned tether from the outside of the aorta. A central stem portion of the sealing element is sufficiently flexible to be pushed away from the locations on the aorta at which suture stitches are inserted during substantial completion 59 of anastomosing the graft vessel to the aorta over the hole in the wall thereof. The central stem portion of the sealing element thus protrudes through the anastomosis between adjacent stitches and is accessible to facilitate removal of the sealing element disposed within the aorta beneath the anastomosis. The sealing element is removed through a tube that is positioned over the central stem portion by applying tensile force to the central stem portion relative to the tube. This disassembles or unravels the sealing element into a single strand 61 that is removed through the tube 63, as shown in FIG. 12. The ends of the suture adjacent to the location on the anastomosis through which the strand was removed may then be tied off to complete the anastomosis 65.

Figure 20:
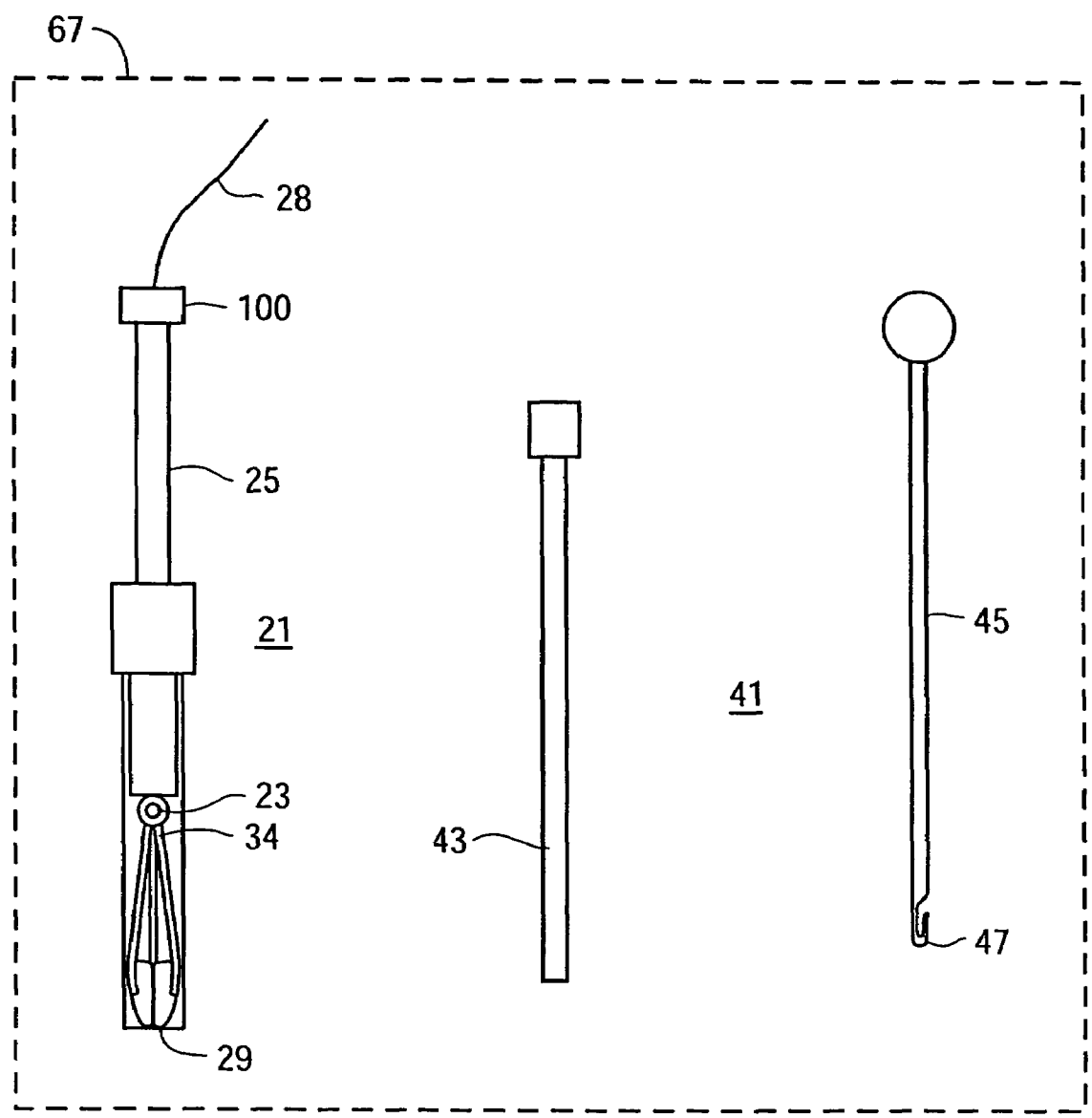
FIG. 20 is a pictorial illustration of a sterile kit of the instruments for performing the surgical process according to the present invention.

Referring now to FIG. 20, there is shown a pictorial illustration of a kit of instruments and components suitable for performing the surgical procedure according to the present invention, as previously described herein. Specifically, at least the seal-insertion instrument 21 and seal removal tube 43 are packaged within a sealed enclosure 67 that preserves a sterile environment and facilitates convenient shipping and handling of these components without contamination or damage. Additionally, a hemostatic sheath 11 may be included within the enclosure 67 for use with a punch (separately available to a surgeon) in the manner as previously described herein with reference to FIGS. 1 and 2.

Therefore, the surgical devices and procedures for forming a temporary aortic seal during proximal anastomosis of a graft vessel to the aorta greatly facilitates removal of the temporary seal with negligible risk of any residual debris being created thereby to circulate in blood flowing in the aorta or in the graft vessel. Additionally, the sealing element of the present invention promotes self sealing of an aortotomy during formation of the vessel graft, aided by a resilient frame that is disposed outside the aorta to support the sealing element during formation of the anastomosis. The resilient frame is easily removed at a convenient stage in the procedure. The sealing element thus positioned to seal off the aortotomy during formation of the anastomosis can be conveniently dissembled into a continuous strand that is pulled from the surgical site with minimal additional trauma or complication of the surgical procedure.

The invention claimed is:

1. A temporary sealing element for forming a fluid-tight seal on the inner wall of a fluid conduit within a patient's body, the temporary sealing element comprising:
    a length of flexible, resilient material integrally forming a stem, and being helically wound to form successive convolutes outwardly from the stem to the periphery, with each convolute adhering to adjacent convolutes along lateral edges thereof to form a fluid impervious flange having the stem centrally formed thereon and including a continuous region of diminished shear strength between adherent convolutes extending from the stem along a continuous path to the periphery for selectively reconfiguring the flange in response to tension applied to the stem to dissemble the flange along the continuous region into a continuous strand;
    a support structure attached to the stem and including a resilient member disposed to expand from a confined configuration of smaller lateral dimension than the periphery of the flange to an expanded configuration of larger lateral dimension than the periphery of the flange; and
    a flexible tether forming the attachment of the stem to mating ends of the resilient member for supporting the stem and attached flange intermediate the mating ends of the resilient member.

2. The temporary sealing element according to claim 1 in which the length of material includes a length of bioinert thermoplastic material forming the stem and flange and including thermoplastic adhesion between lateral edges of adjacent convolutes of the helically-wound length of material.

3. The temporary sealing element according to claim 1 in which the resilient member includes a pair of arms extending to and including the mating ends and resiliently biased for outward extension of the mating ends for tensioning the tether attached thereto.

4. A kit of surgical components for anastomosing a graft vessel on a fluid-carrying vessel using a temporary sealing element for forming a fluid-fight seal on the inner wall of a fluid conduit within a patient's body, the kit comprising:
    a length of flexible, resilient material integrally forming a stem, and being helically wound to form successive convolutes outwardly from the stem to the periphery, with each convolute adhering to adjacent convolutes along lateral edges thereof to form a fluid impervious flange having the stem centrally formed thereon and including a continuous region of diminished shear strength between adherent convolutes extending from the stem along a continuous path to the periphery for selectively reconfiguring the flange in response to tension applied to the stem to dissemble the flange along the continuous region into a continuous strand;
    a support structure attached to the stem and including a resilient member disposed to expand from a confined configuration of smaller lateral dimension than the periphery of the flange to an expanded configuration of larger lateral dimension than the periphery of the flange;
    a flexible tether forming the attachment of the stem to mating ends of the resilient member for supporting the stem and attached flange intermediate the mating ends of the resilient member;

a punch for forming an aperture in a fluid-carrying vessel; and an insertion instrument having an internal bore for incorporating therein the sealing element and support structure in confined orientation for inserting the sealing element through an aperture formable in a fluid-carrying vessel by the punch, the support structure being resiliently expandable out of the insertion instrument and outside the fluid-carrying vessel.

5. The kit according to claim 4 in which the support structure includes a resilient frame separate from the sealing element and includes the flexible tether that is tensioned by the frame and that engages the sealing element in a combined structure of sealing element supported by the tether on the resilient frame.

6. The kit according to claim 5 in which the insertion instrument includes proximal and distal ends, with the combined structure confined within the internal bore near the distal end thereof in compressed configuration of the resilient frame and sealing element for selective deployment therefrom to a configuration that tensions the tether for supporting the sealing element inside a vessel on the resilient frame disposed outside the vessel.

* * * * *